United States Patent [19]

Sohn et al.

[11] Patent Number: 5,319,226
[45] Date of Patent: Jun. 7, 1994

[54] METHOD OF FABRICATING AN ION SENSITIVE FIELD EFFECT TRANSISTOR WITH A TA2O5 HYDROGEN ION SENSING MEMBRANE

[75] Inventors: Byung K. Sohn; Dae H. Kwon, both of Suseong-ku, Rep. of Korea

[73] Assignee: Dong Jin Kim, Seoul, Rep. of Korea

[21] Appl. No.: 846,363

[22] Filed: Mar. 5, 1992

[30] Foreign Application Priority Data

Sep. 6, 1991 [KR] Rep. of Korea ............... 1990-15594

[51] Int. Cl.$^5$ ......................................... H01L 21/265
[52] U.S. Cl. ...................................... 257/253; 437/29; 437/192; 437/235; 437/247; 437/913; 257/414
[58] Field of Search .................. 437/235, 42, 247, 29; 257/253, 414

[56] References Cited

U.S. PATENT DOCUMENTS

| | | | |
|---|---|---|---|
| 3,358,223 | 12/1967 | Birnstingl . | |
| 3,873,361 | 3/1975 | Franco et al. | 117/212 |
| 4,233,033 | 11/1980 | Eifler . | |
| 4,333,808 | 6/1982 | Bhattacharyya | 204/192 |
| 4,374,013 | 2/1983 | Enfors . | |
| 4,385,274 | 5/1983 | Shimada . | |
| 4,495,219 | 1/1985 | Kato et al. | 427/82 |
| 4,513,280 | 4/1985 | Hannan . | |
| 4,657,658 | 4/1987 | Sibbald . | |
| 4,812,220 | 3/1989 | Iida . | |
| 4,839,000 | 6/1989 | Eddowes . | |
| 5,132,012 | 7/1992 | Miura et al. | 210/198.2 |

Primary Examiner—Olik Chaudhuri
Assistant Examiner—H. Jey Tsai

[57] ABSTRACT

A fabricating method of an ion sensitive field effect transistor (ISFET) with a $Ta_2O_5$ hydrogen ion sensing membrane, which comprises the steps of forming $Ta_2O_5$ film with a thickness of about 400 to 500 Å by RF reactive sputtering on a $Si_3N_4/SiO_2$ gate dielectric layer of the pH-ISFET, and annealing the resultant film at about 375° to 450° C. in oxygen gas ambience for about one hour. In forming the $Ta_2O_5$ film on the pH-ISFET, the $Ta_2O_5$ film formed in the area except the gate region of the pH-ISFET is removed by a lift-off process utilizing a positive PR film. The $Ta_2O_5$ gate pH-ISFET according to the present invention has higher sensitivity and more stable operation characteristics than those of the conventional pH-ISFET, while the productivity and stability thereof are greatly improved by effecting a whole wafer process.

20 Claims, 9 Drawing Sheets

FIG. 2-a
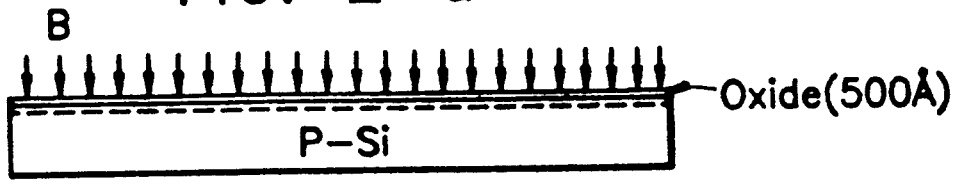
FIG. 2-b
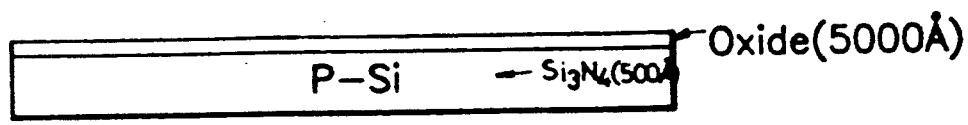
FIG. 2-c
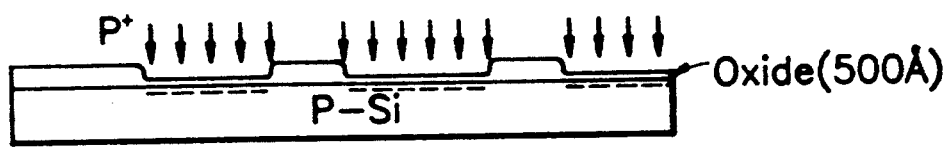
FIG. 2-d
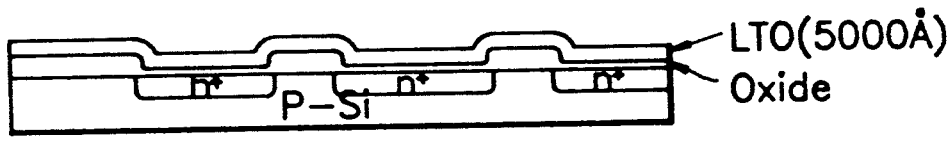
FIG. 2-e
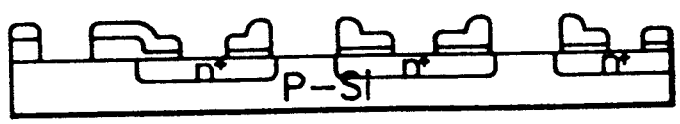

METHOD OF FABRICATING AN ION SENSITIVE FIELD EFFECT TRANSISTOR WITH A TA2O5 HYDROGEN ION SENSING MEMBRANE

BACKGROUND OF THE INVENTION

1. Field of the Invention

The present invention relates to a method of fabricating an ion sensitive field effect transitor (ISFET) with a $Ta_2O_5$ hydrogen ion sensing membrane, and more particularly to a method of fabricating a pH-ISFET with a $Ta_2O_5$ hydrogen ion sensing membrane having high sensitivity and stable operating characteristics.

2. Description of the Prior Art

ISFETs have been developed as a kind of semiconductor ion sensor manufactured by utilizing the manufacturing process of semiconductor integrated circuits and have such characteristics that they are very small in size and light in weight, and thus they can be normally used as ion sensors for in-vivo measurements, being adapted for insertion into the human bloodstream.

Further, the ISFETs have the merits like economic mass production, easy standardization, etc., and thus the ISFET ion sensors can be substituted for existing expensive ion selective electrodes (ISEs). At present, such ISFETs are widely used in the fields of medical treatment, analytical chemistry, environmental management, etc.

The ISFET was firstly reported by P. Bergvelt in 1970, as a result of his preliminary research for an ion sensitive solid-state device for neurophysiological measurements and thereafter, the research was concretely and practically done by Matsuo, Wise, et al.

Table 1 shows sensing characteristics of hydrogen ion sensing membranes of the several pH-ISFETs. According to Table 1, the $SiO_2$ membrane has low sensitivity as well as severe drift, while the $ZrO_2$ membrane has a narrow range of pH measurements, and thus they are not generally used.

In comparison with these membranes, the $Si_3N_4$ membrane can easily be deposited on the gate of the ISFET as a chemically stable dielectric layer, and thus the current leakage through its gate and the hydration in its surface can be reduced, thereby resulting in a stable sensing operation.

However, deterioration in sensing characteristics may be expected in $Si_3N_4$ film depending upon its stoichiometric composition ratio under the specific film depositing condition and storage condition in case that the film is made through low pressure chemical vapor deposition (hereinafter, referred to as LPCVD) process. In other words, under the influence of surface oxidation and non-stoichiometric composition in the film surface, the undesirable hydration may be caused, thereby lowering its sensitivity and greatly increasing the drift.

In order to solve the problem of such disadvantages of $Si_3N_4$ membrane, researches of $Al_2O_3$ and $Ta_2O_5$ thin films which are metal oxides, have been actively carried out.

The $Ta_2O_5$ thin film has much better sensing characteristics than those of other ISFET hydrogen ion sensing membranes and further, it has the advantage that the deterioration of its characteristics due to its surface oxidation are not found, differently from those of the $Si_3N_4$ membrane even when it is exposed to the open air. However, it has the disadvantage that its sensing characteristics would be affected by the film depositing method and its annealing condition.

TABLE 1

(Sensing characteristics of ion sensing membranes of the pH-ISFETs)

| characteristics | sensing membrane | | | | |
|---|---|---|---|---|---|
| | $SiO_2$ | $Si_3N_4$ | $Al_2O_3$ | $ZrO_2$ | $Ta_2O_5$ |
| possible range of pH measurement | 4–10 | 1–13 | 1–13 | 0–8 | 1–13 |
| sensitivity (mV/pH) | 25–35 | 46–56 | 53–58 | 50–58 | 56–58 |
| response time (95%, sec) | 1 | <0.1 | <0.1 | >0.1 | <0.1 |
| long-term stability (mV/h, pH 7) | unstable | 3.0 | 0.8 | stable | 0.2 |

Conventional methods of depositing the $Ta_2O_5$ thin film is divided roughly into two groups; RF sputtering process and chemical vapor deposition (CVD) process.

$Ta_2O_5$ film can be formed by thermal CVD, plasma enhanced CVD (PECVD), photo CVD or low pressure CVD (LPCVD) process among the various CVD processes.

Generally, the CVD processes provide such advantages as the formation of the film in that the film is excellent in its stoichiometric composition and in its productivity. However, the equipment for this process is very expensive and complicated, and thus it is difficult to determine the optimum deposition parameters. Further, it has the disadvantage that the gas to be used is costly and consuming.

On the other hand, the equipment for the RF sputtering process is relatively inexpensive and easy operate according to its simple structure, but this process has the disadvantages that it is difficult to effect the desired stoichiometric composition and to avoid the damage on the film surface caused by its plasma process and resulting lower productivity.

Japanese Patent Laid-open No. 62-245956 published on Oct. 27, 1987 discloses a pH-ISFET sensor in which $Ta_2O_5$ hydrogen ion sensing membrane is deposited by the RF sputtering process.

According to the above-mentioned invention, the $Ta_2O_5$ thin film of the ISFET is deposited by the RF sputtering process, but it is difficult to improve the stoichiometric composition ratio of tantalum and oxygen and this causes a decrease in the sensitivity of the pH-ISFET sensor. In that invention, after deposition step, the film is annealed at a temperature of 275°–300° C. in an inert gas (e.g. nitrogen or argon gas) ambience for 10 minutes. However, its annealing temperature is too low to obtain the desired annealing effect. Also, the $Ta_2O_5$ film lacks oxygen, which means that it suffers from a non-stoichiometric composition ratio. Accordingly, it gives a definitive influence to the sensitivity and stability of the sensor as the sensing mechanism of the ISFET is a kind of site binding depending upon the condition of the sensing membrane surface.

Therefore, under the above-mentioned annealing condition, the sensors undergo undesirable influences in the sensitivity and the stability thereof. Further, during the deposition of the $Ta_2O_5$ thin film, the bonding region of the ISFET except its gate region is covered with a mask and then sputtered. Such process utilizing the mask is not a whole wafer process by photo etching, but is carried out manually, and then it is troublesome in productivity and standardization.

SUMMARY OF THE INVENTION

It is an object of the present invention to provide a fabricating method of a pH-ISFET with a $Ta_2O_5$ hydrogen ion sensing membrane which has higher sensitivity and more stable operating characteristics by improving the stoichiometric composition ratio of the $Ta_2O_5$ sensing membrane.

It is another object of the present invention to provide a method for fabricating a pH-ISFET with a $Ta_2O_5$ hydrogen ion sensing membrane which can enhance productivity and stability of the pH-ISFET by utilizing a whole wafer process.

In order to achieve the above objects, the fabricating method of a pH-ISFET with a $Ta_2O_5$ hydrogen ion sensing membrane according to the present invention comprises the steps of: forming $Ta_2O_5$ film with a thickness of about 400 to 500 Å by RF reactive sputtering on a gate dielectric layer composed of $Si_3N_4$ and $SiO_2$; and annealing the resultant $Ta_2O_5$ film at about 375°–450° C. in $O_2$ ambience for about one hour.

BRIEF DESCRIPTION OF THE DRAWINGS

These and other features of the present invention will now be described in detail with reference to the accompanying drawings, in which;

FIGS. 2A–2I shows fabricating processes of the $Ta_2O_5$ gate pH-ISFET according to the present invention by means of sectional views.

DETAILED DESCRIPTION OF THE PREFERRED EMBODIMENTS

Figure 1:
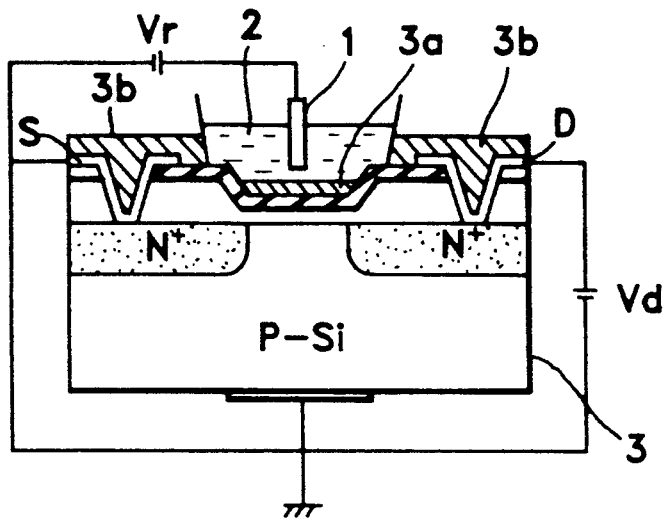
FIG. 1 shows a sectional view of an ion sensitive field effect transistor.

Referring to FIG. 1, an ISFET is a kind of semiconductor ion sensor having the characteristics both the ion sensitivity of an ion selective electrode (ISE) and the field effect of a metal insulator field effect transistor (MISFET). That is, the ISFET has a structure in which the metal gate region of the MISFET is replaced by an ion sensing membrane 3a which reacts upon the hydrogen ion in the solution 2 to be measured, and its operating characteristics are substantially similar to those of the MISFET.

The reference electrode 1 is used to keep the electric potential of the solution 2 constant. When the ISFET 3 is soaked in the solution 2, the $Ta_2O_5$ membrane reacts upon the hydrogen ion in the solution 2, resulting in the change of the hydrogen ion concentration in the $Ta_2O_5$ membrane. This causes the difference in electrochemical potential in the $Ta_2O_5$ membrane and changes the chemical conductance of the ISFET 3. Therefore, the change of the concentration of the hydrogen ion in the solution 2 can be detected as that of the drain current of the ISFET 3.

In FIG. 1, the reference numeral S indicates a source electrode, Vr a reference voltage applied to the reference electrode 1, Vd a drain voltage, and 3b an insulating material respectively.

Figure 2F:
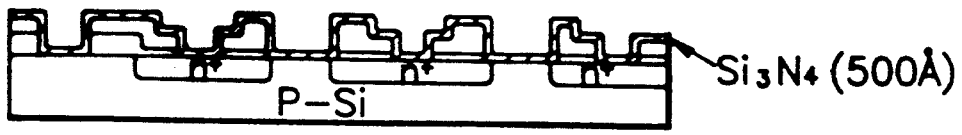
Figure 2G:
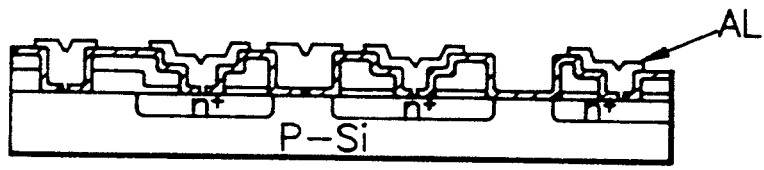
Figure 2H:
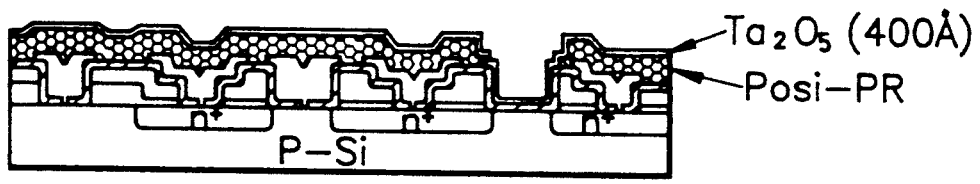
Figure 2I:
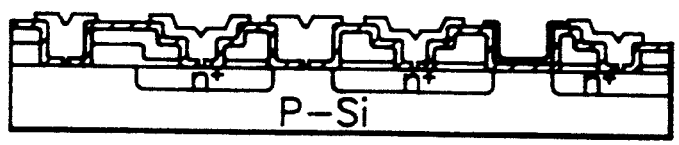

Referring to FIGS. 2A–2I explaining the fabricating processes of the $Ta_2O_5$ gate pH-ISFET, a $Si_3N_4/SiO_2$ gate pH-ISFET is firstly manufactured in the conventional way as shown in FIGS. 2A–2G. Then, $Ta_2O_5$ thin film with a thickness of about 400 to 500 Å is deposited on the ISFET by RF reactive sputtering as shown in FIGS. 2H and 2I, while such RF reactive sputtering condition in order to optimize the stoichiometric composition ratio in the $Ta_2O_5$ thin film is shown in Table 2.

The reason utilizing such reactive sputtering method is for improving the stoichiometric composition ratio in the $Ta_2O_5$ thin film by using gases in plasma ambience composed of Argon and Oxgen gases, since the $Ta_2O_5$ thin film formed by the conventional RF sputtering has a composition ratio which shows an oxygen deficiency.

TABLE 2

| (RF reactive sputtering conditions for the $Ta_2O_5$ thin film formation) | |
|---|---|
| formation variables | formation conditions |
| RF power | 250 W |
| ambient pressure | 3 m torr |
| gas mixing ratio (Ar/$O_2$) | 8:2 SCCM |
| substrate temperature | 120° C. |

In forming such $Ta_2O_5$ thin film, a lift-off process utilizing a positive photosensitive resist (PR) film may be used as shown in FIG. 2H so that the $Ta_2O_5$ thin film formed in the area except the gate region of the pH-ISFET can be removed as shown in FIG. 2I. According to this process, the conventional plasma etching process for etching the $Ta_2O_5$ film is not necessary and thus it is possible to avoid the damage on the film surface and to effect the whole wafer process, so that the productivity and stability of the pH-ISFET can be improved.

EMBODIMENT

The $Ta_2O_5$ thin film was deposited by the RF reactive sputtering on the $Si_3N_4/SiO_2$ gate pH-ISFET which had been manufactured by a conventional way and then annealed at 400° C. in $O_2$ ambience for one hour. The thickness of the $Ta_2O_5$ film deposited was about 450 Å for 30 minutes' sputtering time.

Figure 3:
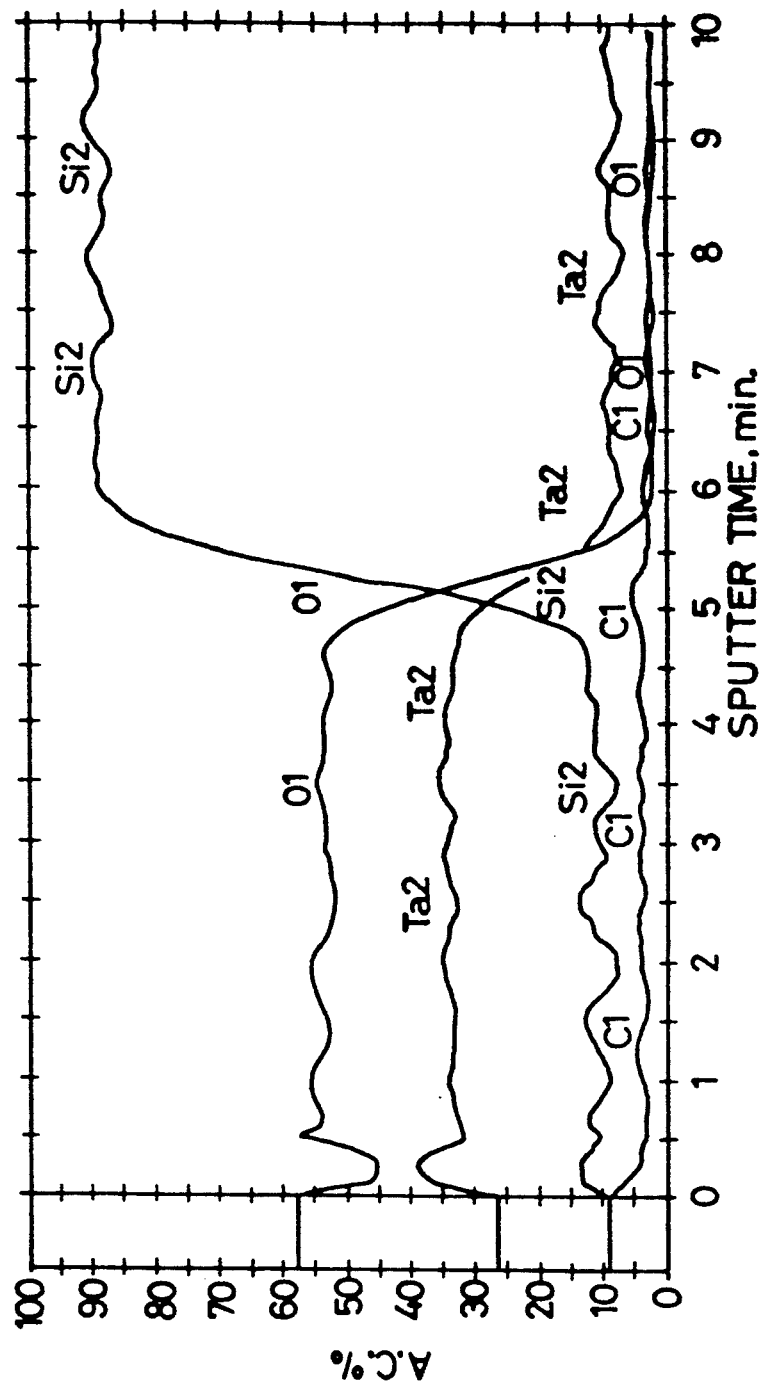
FIG. 3 shows a graph for analyzing AES depth profile of the $Ta_2O_5$ thin film deposited by RF sputtering.
Figure 4:
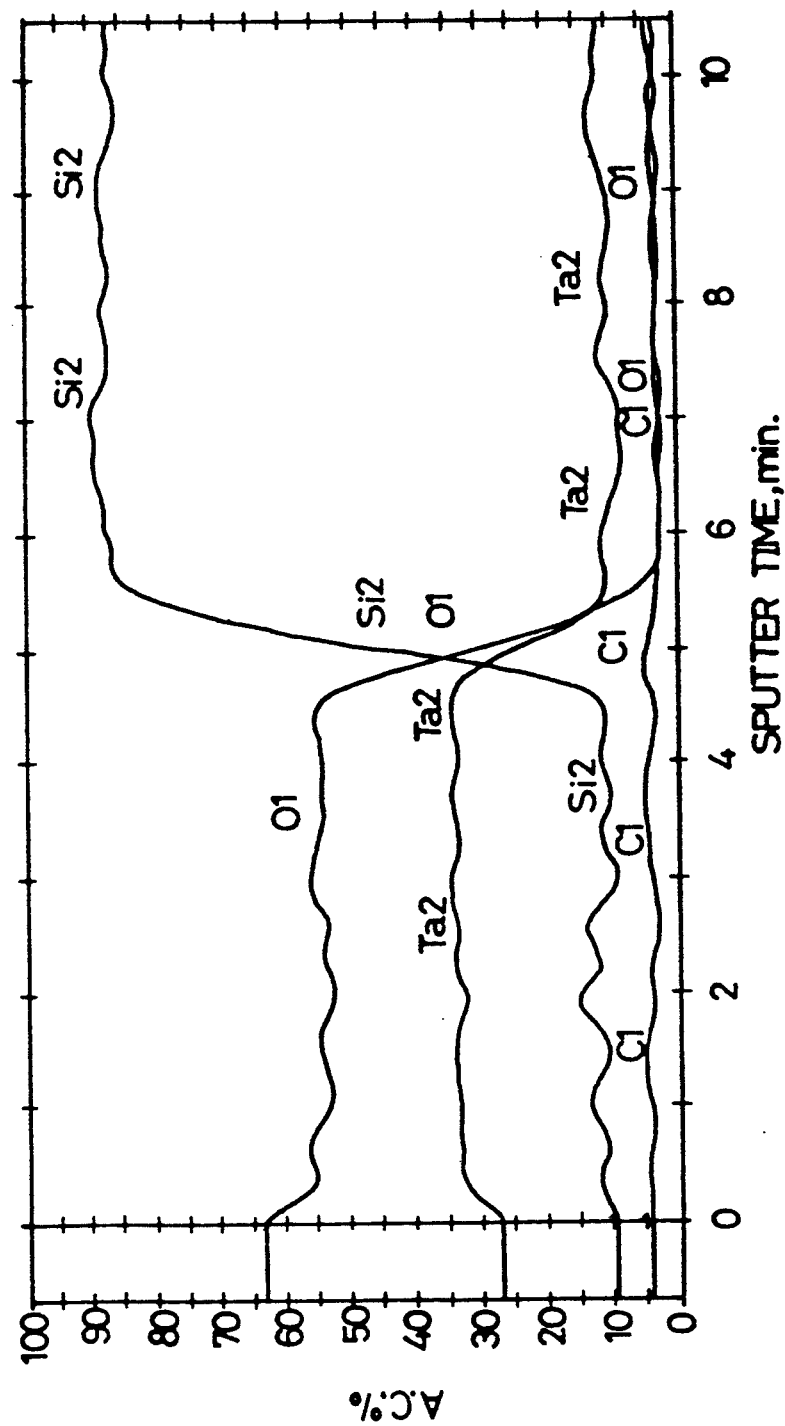
FIG. 4 shows a graph for analyzing AES depth profile of the $Ta_2O_5$ thin film deposited by RF reactive sputtering.

The AES (Auger Election Spectroscopy) analyzing of the $Ta_2O_5$ thin film was carried out as shown in FIG. 4 immediately after forming the film by the RF reactive sputtering. The $Ta_2O_5$ film formed by the RF reactive sputtering showed good stoichiometric composition ratio (Ta/O) in its surface in comparison with that made by the RF sputtering, which shows a serious oxygen deficiency in the composition ratio (Ta/O) in the surface of the film as shown in FIG. 3 illustrating the AES analyzing results of the $Ta_2O_5$ thin film formed by the RF sputtering.

As can be seen from FIGS. 3 and 4, the RF reactive sputtering method rather than the RF sputtering method is desirable in forming the $Ta_2O_5$ hydrogen ion sensing membrane, as the sensibility of the ISFET's ion sensing membrane depend upon the surface condition of the membrane.

Figure 5:
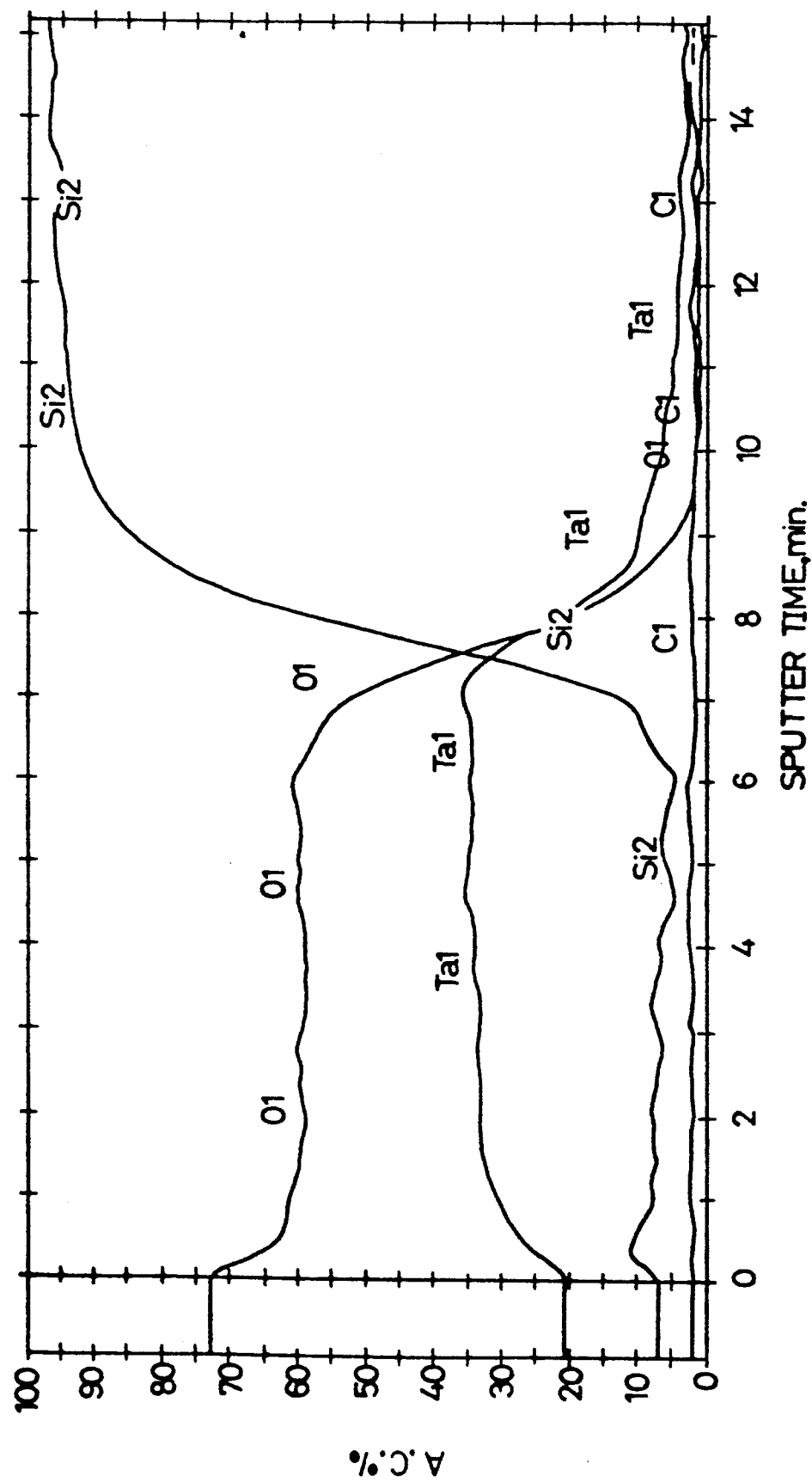
FIG. 5 shows a graph for analyzing AES depth profile of the $Ta_2O_5$ thin film annealed at about 400° C. in $O_2$ ambience for about one hour.

The AES analyzing of the composition of the $Ta_2O_5$ membrane made as described in the above Embodiment was carried out as shown in FIG. 5. The $Ta_2O_5$ membrane annealed in $O_2$ ambience showed good stoichiometric composition ratio (Ta/0=2.5) in its surface as well as in its bulk.

Figure 7:
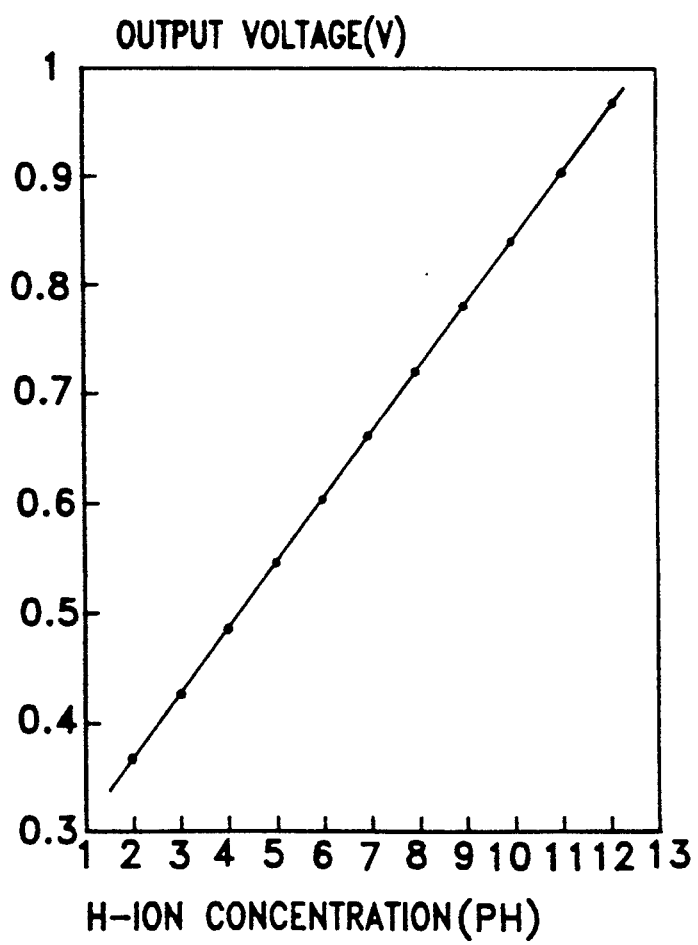
FIG. 7 shows a graph for explaining hydrogen ion sensing characteristics of the $Ta_2O_5$ gate pH-ISFET annealed at about 400° C. in $O_2$ ambience for about one hour.

The hydrogen ion sensing characteristics of the $Ta_2O_5$ gate pH-ISFET formed as described in the above Embodiment were tested as shown in FIG. 7. The $Ta_2O_5$ gate pH-ISFET showed a good linearity in a wide pH range (pH 2 to 12) and a high sensitivity (about 58.7 mV/pH), which is substantially identical with the theoritical value (59 mV/pH) calculated by Nernst equation.

Figure 8:
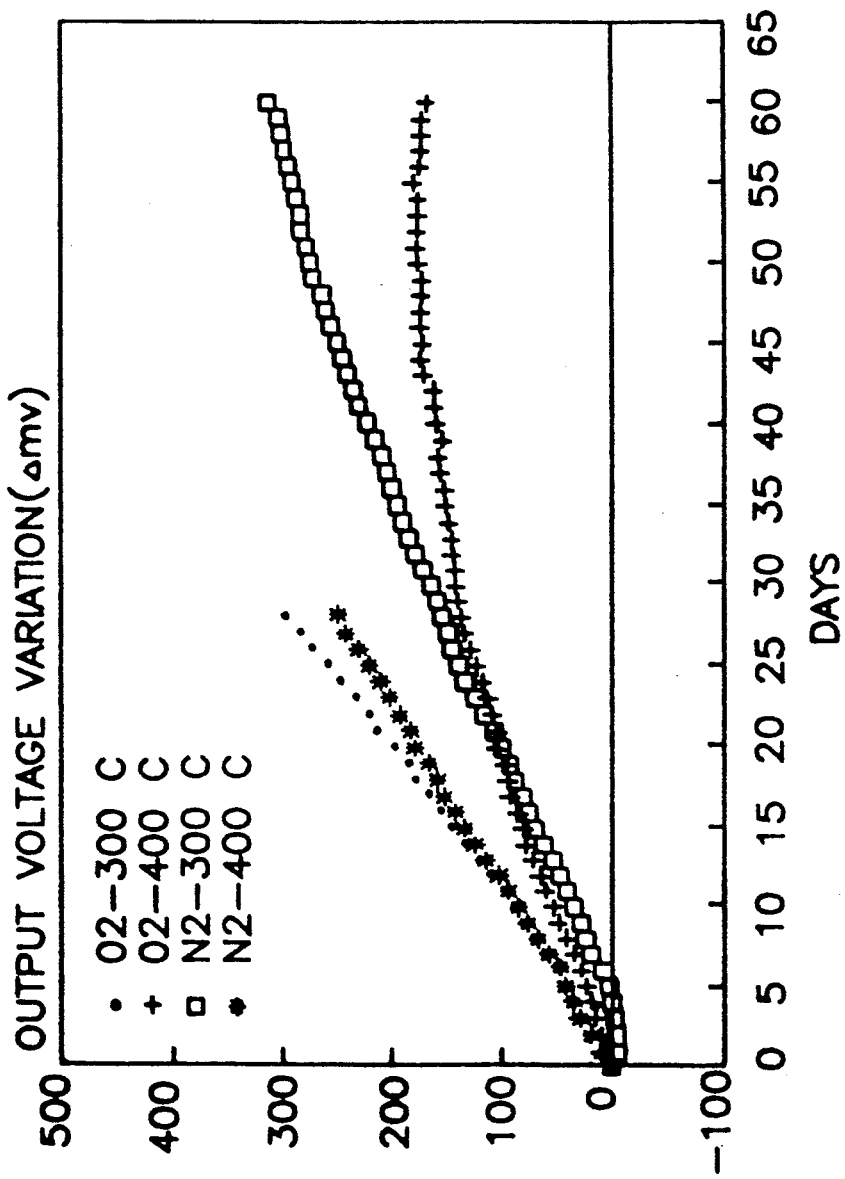
FIG. 8 shows a graph for explaining long-term stabilities of the $Ta_2O_5$ gate pH-ISFET with several annealing temperatures and gases.

The long-term stability of the $Ta_2O_5$ gate pH-ISFET manufactured as described in the Embodiment was measured by Data-logger system and showed in FIG. 8. According to FIG. 8, the long-term stability of the $Ta_2O_5$ gate pH-ISFET turned out excellently as a drift below three mV/day.

Figure 9:
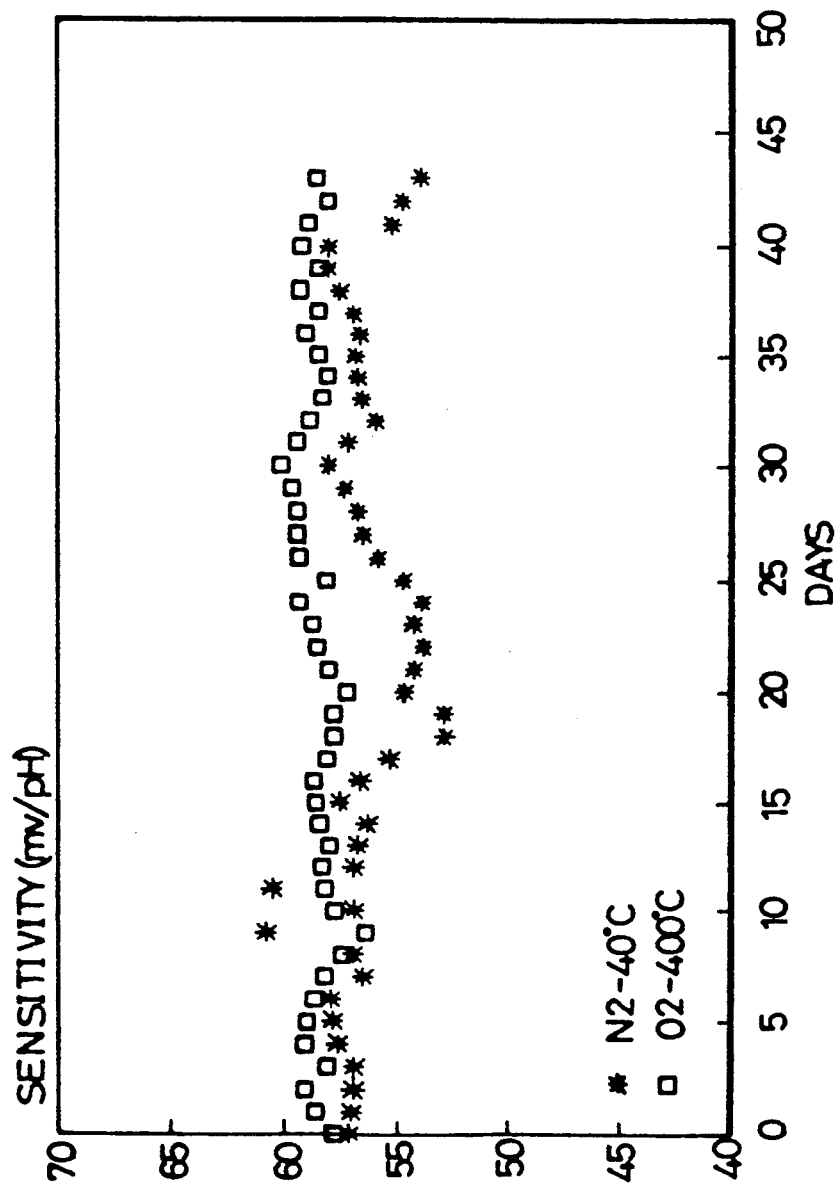
FIG. 9 shows a graph for explaining long-term sensitivities of the $Ta_2O_5$ gate pH-ISFET annealed at about 400° C. $O_2$ and $N_2$ ambiences.

The long-term sensitivity of the $Ta_2O_5$ gate pH-ISFET manufactured as described in the Embodiment was measured and showed in FIG. 9. According to FIG. 9, the sensitivity of the $Ta_2O_5$ gate pH-ISFET showes less variation and high sensitivity (average value of about 58.6 mV/pH).

It has been found that the most suitable thickness of the $Ta_2O_5$ film is 400 to 500 A, considering the dielectric effect and the electric field effect of the film and that the desirable annealing temperature is between 375° and 425° C., taking account of the annealing temperature variation.

CONTROL EXPERIMENTS 1 to 6

The average sensitivities of the $Ta_2O_5$ gate pH-ISFET were tested with various annealing conditions. As can be seen from Table 3, the $Ta_2O_5$ pH-ISFET showed high sensitivities above 55 mV/pH.

TABLE 3

(Average sensitivities of the $Ta_2O_5$ gate pH-ISFETs annealed in Control Experiments)

| Control Experiments | Annealing Conditions | Sensitivities (mV/pH) |
|---|---|---|
| 1 | $O_2$, about 300° C., about 1 hour | 55.9 |
| 2 | $O_2$, about 500° C., about 1 hour | 55.3 |
| 3 | $O_2$, about 600° C., about 1 hour | 55.4 |
| 4 | $O_2$, about 700° C., about 1 hour | 55.3 |
| 5 | $O_2$, about 800° C., about 1 hour | 54.9 |
| 6 | $O_2$, about 900° C., about 1 hour | 53.5 |

The long-term stability of the $Ta_2O_5$ gate pH-ISFET annealed as described in Control Experiment 1 was measured by Data-logger system and showed in FIG. 8. The long-term stability of the $Ta_2O_5$ gate pH-ISFET showed a drift of about 10 mV/day, suggesting unstable operation.

EXPERIMENTAL EXAMPLES 1 to 7

The average sensitivities of the $Ta_2O_5$ gate ISFETs were tested with various annealing temperatures in $N_2$ ambience for one hour and showed in Table 4. In Table 4, the $Ta_2O_5$ gate pH-ISFETs annealed at 300° and 400° C. in $N_2$ ambience for one hour showed high sensitivities (58 mV/pH), but the other $Ta_2O_5$ gate pH-ISFETs annealed at other temperatures showed irregular sensitivities and problems in the long-term stability aspect. It is believed that the current leakage of the $Ta_2O_5$ membrane was increased with increased annealing temperature, due to the phase transition from amorphous to poly-crystal and such leakage current caused a drift of the pH-ISFET.

TABLE 4

(Average sensitivities of the $Ta_2O_5$ gate pH-ISFET annealed in Experimental Examples)

| Experimental Examples | Annealing Conditions | Sensitivities (mV/pH) |
|---|---|---|
| 1 | $N_2$, about 300° C., about 1 hour | 58.0 |
| 2 | $N_2$, about 400° C., about 1 hour | 58.0 |
| 3 | $N_2$, about 500° C., about 1 hour | 53.6 |
| 4 | $N_2$, about 600° C., about 1 hour | 57.1 |
| 5 | $N_2$, about 700° C., about 1 hour | 53.2 |
| 6 | $N_2$, about 800° C., about 1 hour | 56.3 |
| 7 | $N_2$, about 900° C., about 1 hour | 56.8 |

Figure 6:
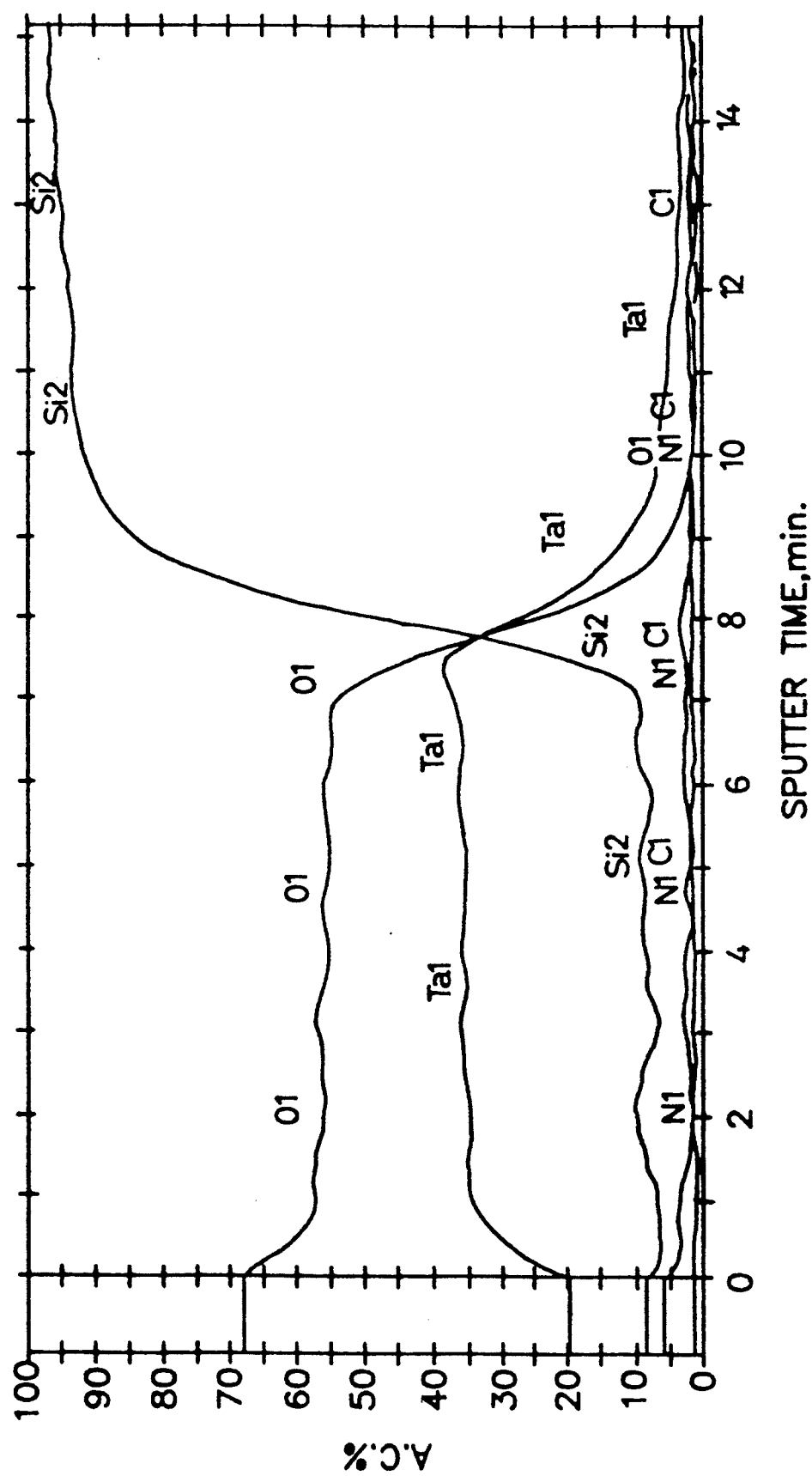
FIG. 6 shows a graph for analyzing AES depth profile of the $Ta_2O_5$ thin film annealed at about 400° C. in $N_2$ ambience for about one hour.

The AES analyzing of the composition of the $Ta_2O_5$ membrane of Experimental Example 2 was carried out as shown in FIG. 6. The $Ta_2O_5$ membrane annealed in $N_2$ ambience showed poor stoichiometric composition ratio in comparison with that of the $Ta_2O_5$ membrane annealed as described in the Embodiment of the present invention.

The long-term stabilities of the $Ta_2O_5$ gate pH-ISFETs annealed as described in Experimental Examples 1 and 2 were measured by Data-logger system and showed in FIG. 8. The long-term stabilities of the $Ta_2O_5$ gate pH-ISFETs of Experimental Examples 1 and 2 showed drifts of about 9 mV/day and 6 mV/day respectively.

The long-term sensitivity of the $Ta_2O_5$ gate pH-ISFET annealed as described in Experimental Example 2 was measured and showed in FIG. 9. The long-term sensitivity annealed in $N_2$ ambience as in Experimental Example 2 showed more variation in sensitivity and lower sensitivity property in comparison with that of the $Ta_2O_5$ gate pH-ISFET of the Embodiment of the present invention.

According to XRD (X-ray diffraction) pattern, the crystal structure of the $Ta_2O_5$ thin film is amorphous at an annealed temperature of less than 500° C. and the phase transition from amorphous to poly-crystal occurs in the vicinity of 500° C. Also, since the current leakage of the $Ta_2O_5$ thin film in the poly-crystal structure is greater than that in the amorphous one, the optimum annealing condition for the best sensing characteristics and the minimum current leakage of the film is effected by the annealing under about 400° C., in $O_2$ ambience and for about one hour. Furthermore, the use of the oxygen as the reactive gas in the annealing step prevents the oxygen deficiency in the surface of the $Ta_2O_5$ thin film as well as supplements oxygen gas in the film surface. According to the above results, the $Ta_2O_5$ gate pH-ISFET annealed at about 400° C. in $O_2$ ambience for 1 hour shows good stoichiometric composition ratio in AES and RBS (Rutherford Backscattering Spectroscopy) analysis.

From the foregoing, it is to be noted that when the $Ta_2O_5$ thin film is used for hydrogen ion sensing membrane of the ISFET, the RF reactive sputtering method rather than the RF sputtering method would be desirable in order to improve the stoichiometric composition ratio of the membrane. Also, a desirable annealing condition would be at the temperature immediately before the phase transition from amorphous to poly-crystal, and in reactive gas($O_2$) ambience rather than in inert gas ambience, so that the resultant $Ta_2O_5$ gate pH-ISFET can have good stoichiometric composition ratio, high sensitivity and excellent long-term stability.

As mentioned above, the fabricating method of the $Ta_2O_5$ gate pH-ISFET according to the present invention is carried out by RF reactive sputtering and annealing in oxygen gas ambience, and thus the resultant $Ta_2O_5$ gate pH-ISFET has high sensitivity and more stable operation characteristics. In particular, according to the present invention, the $Ta_2O_5$ thin film deposited in the area except for the gate region is removed by a lift-off process, so that a whole wafer process can be effected, improving the productivity and stability of the resultant $Ta_2O_5$ gate pH-ISFET.

On the other hand, the $Ta_2O_5$ gate pH-ISFET manufactured by the method according to the present invention can be applied to the hydrogen ion sensor disclosed in Korean Patent Application No. 89-5448 "Microprove for measuring an ion concentration utilizing an ion sensitive field effect transistor" filed by the same inventor, thereby enabling to measure quickly and accurately hydrogen ion concentration in a solution or the human bloodstream.

While the present invention has been described and illustrated herein with rererence to the preferred embodiment thereof, it will be understood by those skilled in the art that various changes in form and details may be made therein without departing from the spirit and scope of the invention.

What is claimed is:

1. A method of fabricating an ion sensitive field effect transistor with a $Ta_2O_5$ hydrogen ion sensing membrane, comprising the steps of:
    forming a $Si_3N_4/SiO_2$ dielectric layer over a gate region of said ion sensitive field effect transistor;
    depositing a film of $Ta_2O_5$ having a thickness of about 400 to 500 Å on said $Si_3N_4/SiO_2$ dielectric layer on said ion sensitive field effect transistor; and
    annealing the resultant film at a temperature of about 375° to 450° C. in oxygen gas ambience.

2. The method according to claim 1, wherein said film of $Ta_2O_5$ is deposited by RF reactive sputtering.

3. The method according to claim 1, wherein said film of $Ta_2O_5$ formed in the areas surrounding said gate region of said ion sensitive field effect transistor are removed by a lift-off process utilizing a positive photosensitive film during a formation of said film of $Ta_2O_5$ on said ion sensitive field effect transistor with said $Si_3N_4/SiO_2$ gate dielectric layer.

4. An ion sensitive field-effect transistor, comprising:
    a semiconductor substrate of a first conductivity type having first and second diffusion regions of a second conductivity type separated and spaced-apart by a gate region, said first and second diffusion regions respectively defining a source region and a drain region;
    a dielectric layer positioned upon the surface of said semiconductor substrate covering said source region, said gate region and said drain region;
    an ion sensitive membrane formed on the dielectric layer over said gate region, said ion sensitive membrane being a $Ta_2O_5$ compound having a thickness of approximately 400–500 Å; and
    first and second metal layers formed in V-shape and positioned upon the dielectric layer over said source region and said drain region, each of said first and second metal layers having a base at a center of one of said source region and said drain region.

5. The ion sensitive field-effect transistors as claimed in claim 4, wherein said ion sensitive membrane is formed on the dielectric layer by RF reactive sputtering and annealing at a temperature in the range of 300° to 900° C. in a reactive oxygen gas ambience for approximately one hour.

6. The ion sensitive field-effect transistor as claimed in claim 5, wherein the range of temperature of the annealing is prefer to be of 375° to 425° C. in a reactive oxygen gas ambience for approximately one hour.

7. The ion sensitive field-effect transistor as claimed in claim 4, wherein said ion sensitive membrane is formed on the dielectric layer by RF reactive sputtering and annealing at a temperature in the range of 375° to 400° C. in a reactive oxygen gas ambience for approximately one hour.

8. The method according to claim 1, wherein the temperature of the annealing of approximately 400° in a reactive oxygen gas ambience for approximately one hour.

9. The ion sensitive field-effect transistor as claimed in claim 4, wherein the temperature of the annealing is preferred to be of approximately 400° C. in a reactive oxygen gas ambience for approximately one hour.

10. A method of fabricating an ion sensitive field effect transistor on a semiconductor substrate of a first conductivity type having first and second diffusion regions of a second conductivity type separated and spaced-apart by a gate region, said first and second diffusion regions respectively defining a source region and a drain region, comprising the steps of:
    forming a dielectric layer over the surface of said semiconductor substrate covering said source region, said gate region and said drain region;
    forming first and second metal layers in V-shape positioned upon the dielectric layer over said source region and said drain region, each of said first and second metal layers having a base at a center of one of said source region and said drain region;
    depositing an ion sensitive layer of $Ta_2O_5$ compound having a thickness of approximately 400–500 Å on the dielectric layer over said gate region; and
    annealing said ion sensitive layer of $Ta_2O_5$ compound at a temperature in the range of 375° to 425° C. in a reactive gas ambience.

11. The method of fabricating an ion sensitive field effect transistor as claimed in claim 10, wherein said reactive gas ambience is oxygen.

12. The method of fabricating an ion sensitive field effect transistor as claimed in claim 10, wherein said ion sensitive layer is deposited by RF reactive sputtering.

13. The method of fabricating an ion sensitive field effect transistor as claimed in claim 10, wherein said ion sensitive layer is annealed in said reactive gas ambience for approximately one hour.

14. The method of fabricating an ion sensitive field effect transistor as claimed in claim 10, wherein the temperature of the annealing is approximately at 400° C.

in said reactive gas ambience of oxygen for approximately one hour.

15. A method of fabricating an ion sensitive field effect transistor on a semiconductor substrate of a first conductivity type having first and second diffusion regions of a second conductivity type separated and spaced-apart by a gate region, each of said first and second diffusion regions respectively defining a source region and a drain region, comprising the steps of:
    forming an insulation layer over the surface of said semiconductor substrate covering said source region, said gate region and said drain region;
    forming first and second metal layers in a V-shape, positioned upon the insulation layer over said source region and said drain region, each of said first and second metal layers having a base at a center of each of said source and drain regions, and a channel having two ends extending in opposite directions away from the center of each of said source and drain regions;
    depositing a photoresist layer on the surface of said first and second metal layers, thereby exposing said gate region;
    sputtering a film of $Ta_2O_5$ having a thickness of approximately 400–500 Å over the surface of said photoresist layer and said gate region in a first gas ambience; and
    removing said photoresist layer, thereby exposing the film of $Ta_2O_5$ having a thickness of approximately 400–500 Å over said gate region; and
    annealing said semiconductor substrate having said film of $Ta_2O_5$ over the gate region in a second gas ambience.

16. The method of fabricating an ion sensitive field effect transistor as claimed in claim 15, wherein said first gas ambience comprises argon and oxygen and said second gas ambience comprises oxygen, and said film of $Ta_2O_5$ is being annealed in said second gas ambience for approximately one hour.

17. The method of fabricating an ion sensitive field effect transistor as claimed in claim 15, wherein said film of $Ta_2O_5$ is being annealed at a temperature range of approximately 375° to 425° C.

18. The method of fabricating an ion sensitive field effect transistor as claimed in claim 16, wherein said film of $Ta_2O_5$ is being annealed at a temperature range of approximately 400° C. in said second gas ambience of oxygen for approximately one hour.

19. An ion sensitive field effect transistor, comprising:
    a semiconductor substrate of a first conductivity type having first and second diffusion regions of a second conductivity type separated and spaced-apart by a gate region, each of said first and second diffusion regions respectively defining a source region and a drain region;
    an insulation layer disposed over the surface of said semiconductor substrate covering said source region, said gate region and said drain region;
    first and second metal layers positioned upon the insulation layer over said source region and said drain region, each of said first and second metal layers having a base at a center of each of said source and drain regions, and a channel having two ends extending in opposite directions away from the center of each of said source and drain regions; and
    an ion sensitive layer of $Ta_2O_5$ having a thickness of approximately 400–500 Å disposed on the insulation layer over the gate region, wherein said ion sensitive layer being disposed on said insulation layer over the gate region comprises the steps of:
        depositing a photoresist layer on the surface of said first and second metal layers, thereby exposing said gate region;
        sputtering said ion sensitive layer of $Ta_2O_5$ having a thickness of approximately 400–500 Å over the surface of said photoresist layer and said gate region in a first gas ambience of argon and oxygen; and
        removing said photoresist layer, thereby exposing said ion sensitive layer of $Ta_2O_5$ having a thickness of approximately 400–500 Å over said gate region; and
        annealing said semiconductor substrate having said ion sensitive layer of $Ta_2O_5$ over the gate region in a second gas ambience of oxygen.

20. The ion sensitive field effect transistor as claimed in claim 19, wherein said ion sensitive layer of $Ta_2O_5$ is annealed in said second gas ambience for approximately one hour at a temperature range of 375° to 425° C.

* * * * *

UNITED STATES PATENT AND TRADEMARK OFFICE
CERTIFICATE OF CORRECTION

PATENT NO. : 5,319,226
DATED : 7 June 1994
INVENTOR(S) : Byung-Ki Sohn, et al.

It is certified that error appears in the above-indentified patent and that said Letters Patent is hereby corrected as shown below:

On the title page, item [54] and column 1, line 4, in the title change "TA2O5" to --$Ta_2O_5$--;

On the title page, item [73], after "Korea", insert --(part interest)--.

On the title page, after item [57] Abstract,

IN THE ATTORNEY'S NAME please insert --*Attorney, Agent, or firm* - Robert E. Bushnell--;

Column 1,

Line 3, change "TA2O5 " to --$Ta_2O_5$--;

UNITED STATES PATENT AND TRADEMARK OFFICE
CERTIFICATE OF CORRECTION

PATENT NO. : 5,319,226
DATED : 7 June 1994
INVENTOR(S) : Byung-Ki Sohn, et al.

Page 2 of 3

It is certified that error appears in the above-indentified patent and that said Letters Patent is hereby corrected as shown below:

Column 4,

Line 28,    change "Oxgen" to --Oxygen--;

Column 5,

Line 32,    change "showes" to --showed--;

Column 7,

Line 32,    change "rererence" to --reference--;

IN THE CLAIMS

Column 7,

Line 44,    change "on" to --of--;

Column 8,

Line 17,    change "prefer" to --preferred--;

Line 27,    after "annealing" insert --is preferred to be--;

UNITED STATES PATENT AND TRADEMARK OFFICE
CERTIFICATE OF CORRECTION

PATENT NO. : 5,319,226
DATED : 7 June 1994
INVENTOR(S) : Byung-Ki Sohn, et al.

It is certified that error appears in the above-indentified patent and that said Letters Patent is hereby corrected as shown below:

Column 10,

Line 43,    after "wherein", insert --said first gas ambience comprises argon and oxygen and said second gas ambience comprises oxygen, and--.

Signed and Sealed this

Third Day of January, 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,319,226

DATED : June 7, 1994

INVENTOR(S) : Byung K. Sohn, et al.

It is certified that error appears in the above-indentified patent and that said Letters Patent is hereby corrected as shown below:

```
The sheets of drawings, consisting of figures 8 and 9, should be
deleted to appear as per attached sheets.
```

Signed and Sealed this

Thirtieth Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,319,226
DATED : 7 June 1994
INVENTOR(S) : SOHN, et al.

It is certified that error appears in the above-indentified patent and that said Letters Patent is hereby corrected as shown below:

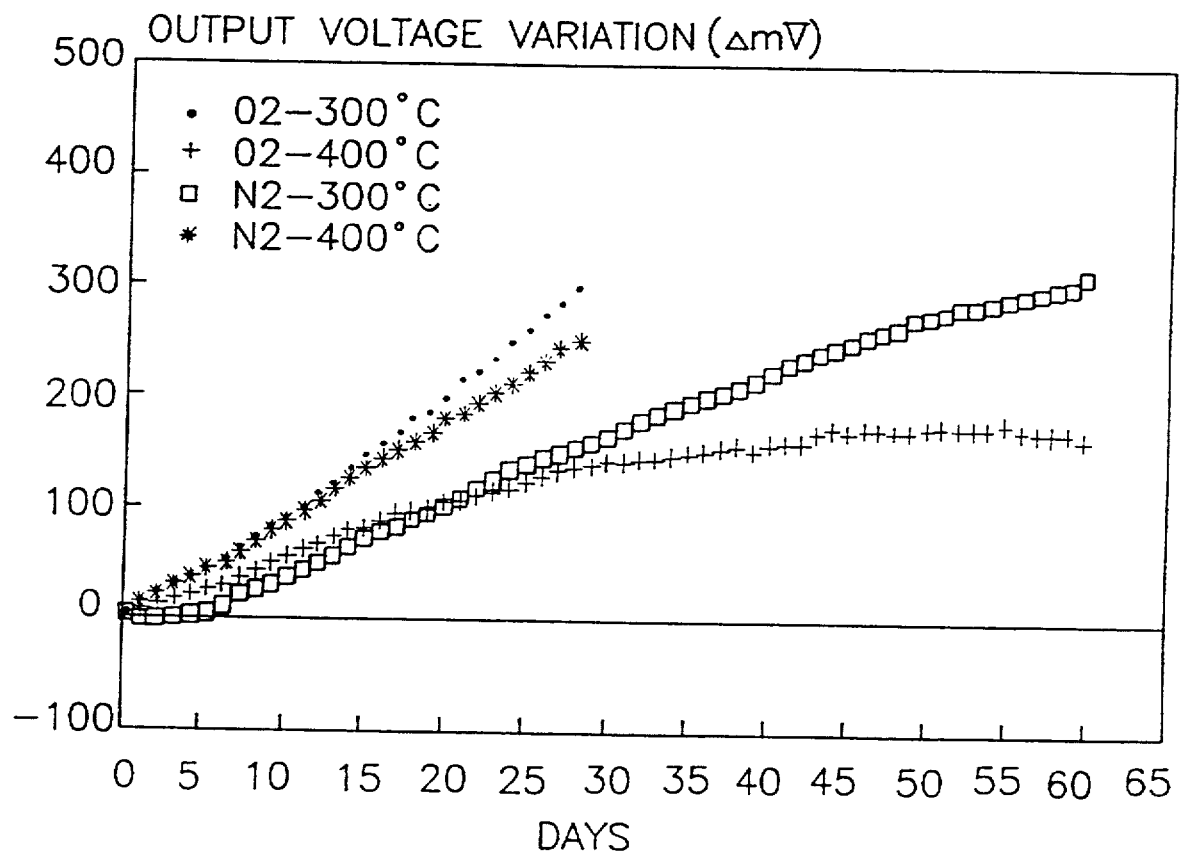

FIG. 8

UNITED STATES PATENT AND TRADEMARK OFFICE
CERTIFICATE OF CORRECTION

PATENT NO. : 5,319,226
DATED : 7 June 1994
INVENTOR(S) : SOHN, et al.

Page 3 of 3

It is certified that error appears in the above-indentified patent and that said Letters Patent is hereby corrected as shown below:

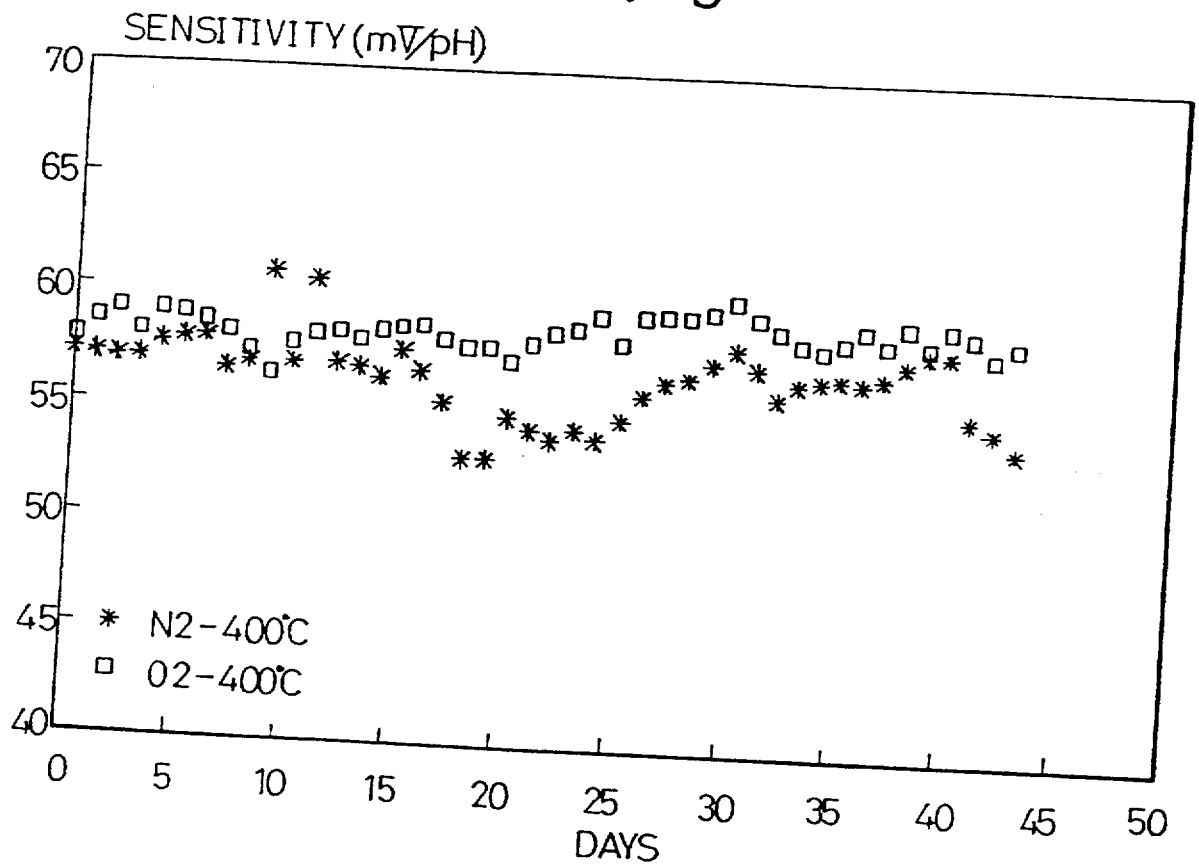

FIG. 9